US010384025B2

(12) United States Patent
Fox et al.

(10) Patent No.: US 10,384,025 B2
(45) Date of Patent: Aug. 20, 2019

(54) SYSTEM AND METHOD FOR LIMITING FLOW AND/OR PRESSURE COMPENSATION DURING LIMITED FLOW RESPIRATORY THERAPY

(71) Applicant: KONINKLIJKE PHILIPS N.V., Eindhoven (NL)

(72) Inventors: Nathaniel Solomon Fox, Pittsburgh, PA (US); Manuel Laura Lapoint, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 657 days.

(21) Appl. No.: 14/648,999

(22) PCT Filed: Dec. 17, 2013

(86) PCT No.: PCT/IB2013/061012
§ 371 (c)(1),
(2) Date: Jun. 2, 2015

(87) PCT Pub. No.: WO2014/102659
PCT Pub. Date: Jul. 3, 2014

(65) Prior Publication Data
US 2015/0314091 A1 Nov. 5, 2015

Related U.S. Application Data

(60) Provisional application No. 61/745,870, filed on Dec. 26, 2012.

(51) Int. Cl.
*A61M 16/00* (2006.01)
*A61M 16/10* (2006.01)
(Continued)

(52) U.S. Cl.
CPC ......... *A61M 16/024* (2017.08); *A61B 5/4836* (2013.01); *A61M 16/0057* (2013.01);
(Continued)

(58) Field of Classification Search
CPC ...... A61M 2205/15; A61M 2205/3334; A61M 2016/003; A61M 2016/0015; A61M 2016/0027; A61M 16/201
See application file for complete search history.

(56) References Cited

U.S. PATENT DOCUMENTS 5,632,269 A * 5/1997 Zdrojkowski ....... A61M 16/026
128/204.21
6,626,175 B2 9/2003 Jafari et al.
(Continued)

FOREIGN PATENT DOCUMENTS

RU 2185196 C2 7/2002
WO 2005051469 A1 6/2005
(Continued)

*Primary Examiner* — Colin W Stuart
*Assistant Examiner* — Douglas Y Sul

(57) ABSTRACT

A pressure support system configured to deliver a pressurized flow of breathable gas to the airway of a subject is described. The system is configured to treat obstructive sleep apnea, other sleep disordered breathing, and/or other respiratory issues with limited flow respiration therapy, and/or other therapies. Limited flow respiration therapy may be an alternative to CPAP, for example. The system is configured to limit flow rate compensation, pressure compensation, and/generator or compensation of other parameters during inspiration to values proportional to the current leak to achieve limited flow respiration therapy. In some embodiments, the system comprises one or more of a pressure generator, a subject interface, one or more sensors, a processor, a user interface, electronic storage, and/or other components.

21 Claims, 2 Drawing Sheets

(51) Int. Cl.
- *A61B 5/08* (2006.01)
- *A61B 5/087* (2006.01)
- *A61B 5/091* (2006.01)
- *A61B 5/00* (2006.01)
- *A61M 16/16* (2006.01)
- *A61M 16/20* (2006.01)

(52) U.S. Cl.
CPC ......... *A61M 16/0069* (2014.02); *A61B 5/082* (2013.01); *A61B 5/087* (2013.01); *A61B 5/0816* (2013.01); *A61B 5/091* (2013.01); *A61M 16/161* (2014.02); *A61M 16/201* (2014.02); *A61M 2016/003* (2013.01); *A61M 2016/0015* (2013.01); *A61M 2016/0027* (2013.01); *A61M 2016/102* (2013.01); *A61M 2205/15* (2013.01); *A61M 2205/3331* (2013.01); *A61M 2205/3365* (2013.01); *A61M 2205/3368* (2013.01); *A61M 2205/3375* (2013.01); *A61M 2205/502* (2013.01); *A61M 2205/52* (2013.01)

(56) References Cited

U.S. PATENT DOCUMENTS

| | | | |
|---|---|---|---|
| 6,920,875 | B1 | 7/2005 | Hill et al. |
| 2002/0014240 | A1* | 2/2002 | Truschel ........... A61M 16/0051 128/204.22 |
| 2006/0000475 | A1* | 1/2006 | Matthews ......... A61M 16/0051 128/204.21 |
| 2008/0295837 | A1* | 12/2008 | McCormick ...... A61M 16/0051 128/204.21 |
| 2010/0147303 | A1* | 6/2010 | Jafari ................ A61M 16/0051 128/204.23 |
| 2013/0131577 | A1 | 5/2013 | Bronstein |
| 2013/0167842 | A1* | 7/2013 | Jafari .................... A61M 16/00 128/204.21 |
| 2014/0109910 | A1 | 4/2014 | Colbaugh |
| 2015/0314091 | A1 | 11/2015 | Fox et al. |

FOREIGN PATENT DOCUMENTS

| | | |
|---|---|---|
| WO | 2008100859 A2 | 12/2008 |
| WO | 2009112076 A1 | 9/2009 |

* cited by examiner

SYSTEM AND METHOD FOR LIMITING FLOW AND/OR PRESSURE COMPENSATION DURING LIMITED FLOW RESPIRATORY THERAPY

CROSS-REFERENCE TO PRIOR APPLICATIONS

This application is the U.S. National Phase application under 35 U.S.C. § 371 of International Application Serial No. PCT/IB2013/061012, filed on Dec. 17, 2013, which claims the benefit of U.S. Application Ser. No. 61/745,870, filed on Dec. 26, 2012. These applications are hereby incorporated by reference herein.

The present disclosure pertains to a pressure support system configured to deliver a pressurized flow of breathable gas to the airway of a subject. The pressure support system is configured to determine a compensation limit for a compensation amount of a gas parameter based on a current leak value.

Systems to treat obstructive sleep apnea (OSA) are known. Typically, OSA is treated via positive airway pressure (PAP). There are multiple methods available to deliver PAP. The most common method is continuous positive airway pressure (CPAP). Traditional therapies may be uncomfortable for some patients. Breathing in while air is being forced into the airway using positive airway pressure may feel uncomfortable and/or unnatural to some patients.

Accordingly, one or more aspects of the present disclosure relate to a pressure support system configured to deliver a pressurized flow of breathable gas to the airway of a subject. The pressure support system comprises a pressure generator, one or more sensors, and one or more processors. The pressure generator is configured to generate the pressurized flow of breathable gas. The one or more sensors are configured to generate output signals conveying information related to one or more gas parameters of the pressurized flow of breathable gas. The one or more processors are configured to execute computer program modules. The computer program modules comprise a leak module, a control module, a compensation module, and a compensation limit module. The leak module is configured to estimate a current leak value. The control module is configured to control operation of the pressure generator to generate the pressurized flow of breathable gas according to a limited flow mode therapy regime that dictates a therapeutic level of a first gas parameter of the one or more gas parameters at or near the airway of the subject. The compensation module is configured to determine a compensation amount to adjust the first gas parameter to compensate for respiratory effort during inhalation to maintain the therapeutic level for the first gas parameter. The compensation module is configured to determine the compensation amount based on the therapeutic level and the output signals. The control module is configured to control the pressure generator to generate the pressurized flow of breathable gas with the first gas parameter at a level that reflects the compensation amount. The compensation limit module is configured to determine a compensation limit for the compensation amount of the first gas parameter based on the current leak value. The compensation module is configured to implement the compensation limit as a limit for the compensation amount.

Yet another aspect of the present disclosure relates to a method for delivering a pressurized flow of breathable gas to the airway of a subject with a pressure support system. The pressure support system comprises a pressure generator, one or more sensors, and one or more processors. The one or more processors are configured to execute computer program modules. The computer program modules comprise a leak module, a control module, a compensation module, and a compensation limit module. The method comprises generating the pressurized flow of breathable gas with the pressure generator; generating output signals conveying information related to one or more gas parameters of the pressurized flow of breathable gas with the one or more sensors; estimating a current leak value with the leak module; controlling, with the control module, operation of the pressure generator to generate the pressurized flow of breathable gas according to a limited flow mode therapy regime that dictates a therapeutic level of a first gas parameter of the one or more gas parameters at or near the airway of the subject; determining a compensation amount, with the compensation module, to adjust the first gas parameter to compensate for respiratory effort during inhalation to maintain the therapeutic level for the first gas parameter, wherein determining the compensation amount is based on the therapeutic level and the output signals; controlling, with the control module, generation of the pressurized flow of breathable gas with the first gas parameter at a level that reflects the compensation amount; determining a compensation limit, with the compensation limit module, for the compensation amount of the first gas parameter based on the current leak value; and implementing, with the compensation module, the compensation limit as a limit for the compensation amount.

Still another aspect of the present disclosure relates to a pressure support system configured to deliver a pressurized flow of breathable gas to the airway of a subject. The pressure support system comprises means for generating the pressurized flow of breathable gas; means for generating output signals conveying information related to one or more gas parameters of the pressurized flow of breathable gas; and means for executing computer program modules. The computer program modules comprise means for estimating a current leak value; means for controlling operation of the means for generating the pressurized flow of breathable gas to generate the pressurized flow of breathable gas according to a limited flow mode therapy regime that dictates a therapeutic level of a first gas parameter of the one or more gas parameters at or near the airway of the subject; means for determining a compensation amount to adjust the first gas parameter to compensate for respiratory effort during inhalation to maintain the therapeutic level for the first gas parameter, wherein the means for determining a compensation amount is configured to determine the compensation amount based on the therapeutic level and the output signals, wherein the means for controlling operation is configured to control the means for generating the pressurized flow of breathable gas to generate the pressurized flow of breathable gas with the first gas parameter at a level that reflects the compensation amount; and means for determining a compensation limit for the compensation amount of the first gas parameter based on the current leak value, wherein the means for determining a compensation is configured to implement the compensation limit as a limit for the compensation amount.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

Figure 1:
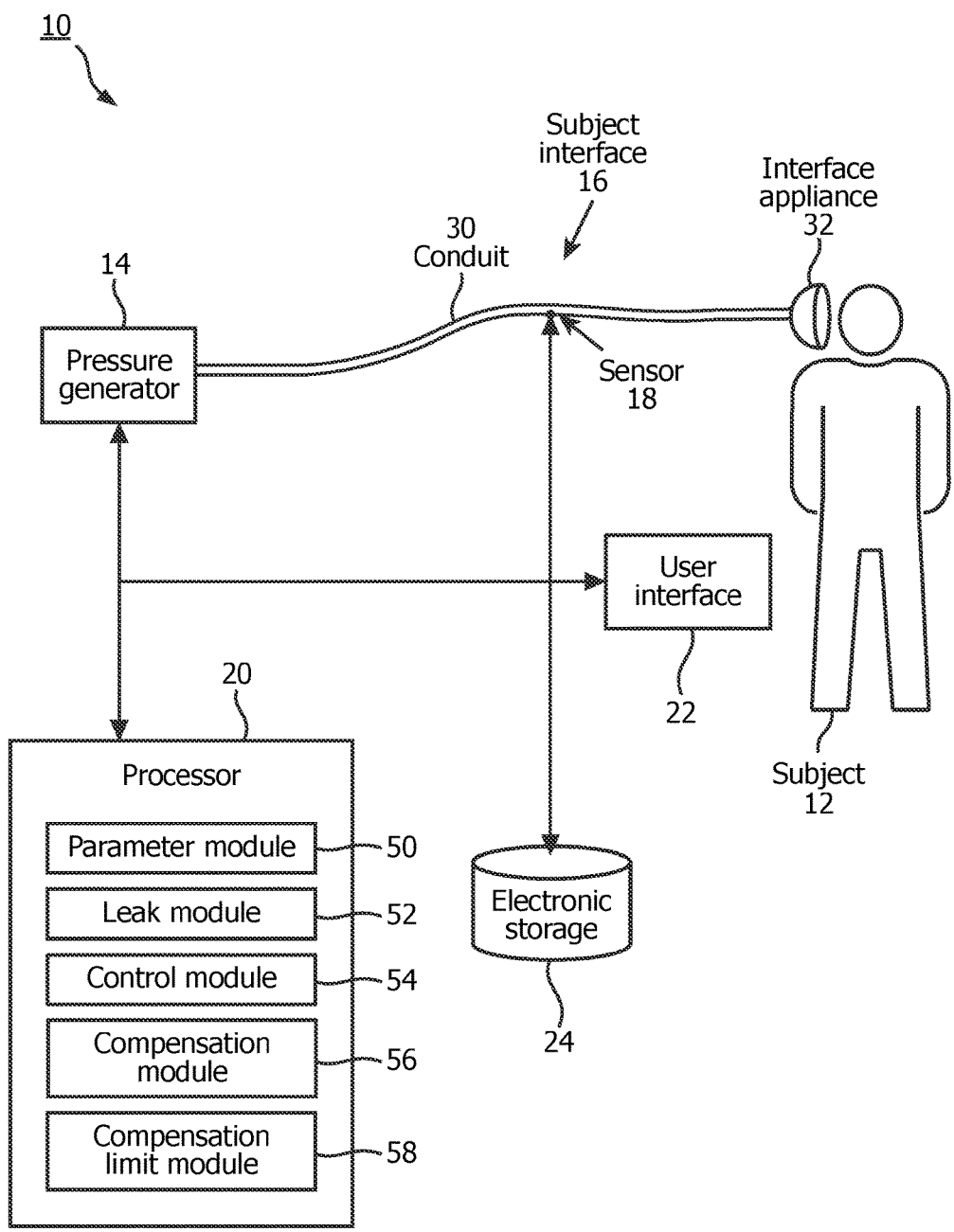
FIG. 1 is a schematic illustration of a pressure support system configured to deliver a pressurized flow of breathable gas to the airway of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a pressure support system 10 configured to deliver a pressurized flow of breathable gas to the airway of a subject 12. System 10 is configured to treat obstructive sleep apnea, other sleep disordered breathing, and/or other respiratory issues with limited flow respiration therapy, and/or other therapies. Limited flow respiration therapy may be an alternative to CPAP, for example. Limited flow respiration therapy is described in U.S. Patent Application No. 61/503,634, filed Jul. 1, 2011, entitled "System and Method for Limited Flow Respiration Therapy", incorporated herein by reference. System 10 is configured to limit flow rate compensation, pressure compensation, and/or other parameters during inspiration to values proportional to the current leak to achieve limited flow respiration therapy. In some embodiments, system 10 comprises one or more of a pressure generator 14, a subject interface 16, one or more sensors 18, a processor 20, a user interface 22, electronic storage 24, and/or other components.

Pressure generator 14 is configured to generate a pressurized flow of breathable gas for delivery to the airway of subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate, the pressure, and/or other parameters of the flow of gas to provide limited flow respiration therapy to the airway of subject 12.

Pressure generator 14 receives a flow of gas from a gas source, such as the ambient atmosphere, and elevates and/or reduces the pressure of that gas for delivery to the airway of a patient. Pressure generator 14 is any device, such as, for example, a pump, blower, piston, or bellows, that is capable of elevating and/or reducing the pressure of the received gas for delivery to a patient. Pressure generator 14 may comprise one or more valves for controlling the pressure and/or flow of gas, for example. The present disclosure also contemplates controlling the operating speed of the blower, either alone or in combination with such valves, to control the pressure and/or flow of gas provided to the patient.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit, that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Sensors 18 are configured to generate output signals conveying information related to one or more gas parameters of the pressurized flow of breathable gas. The one or more gas parameters may comprise one or more of a flow rate, a volume, a pressure, a composition (e.g., concentration(s) of one or more constituents), temperature, humidity, acceleration, velocity, acoustics, changes in a parameter indicative of respiratory effort by subject 12, and/or other gas parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters). Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, in communication with subject 12, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG.

1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program modules. The one or more computer program modules may comprise one or more of a parameter module 50, a leak module 52, a control module 54, a compensation module 56, a compensation limit module 58, and/or other modules. Processor 20 may be configured to execute modules 50, 52, 54, 56, and/or 58 by software; hardware; firmware; some combination of software, hardware, and/or firmware; and/or other mechanisms for configuring processing capabilities on processor 20.

It should be appreciated that although modules 50, 52, 54, 56, and 58 are illustrated in FIG. 1 as being co-located within a single processing unit, in implementations in which processor 20 comprises multiple processing units, one or more of modules 50, 52, 54, 56, and/or 58 may be located remotely from the other modules. The description of the functionality provided by the different modules 50, 52, 54, 56, and/or 58 described below is for illustrative purposes, and is not intended to be limiting, as any of modules 50, 52, 54, 56, and/or 58 may provide more or less functionality than is described. For example, one or more of modules 50, 52, 54, 56, and/or 58 may be eliminated, and some or all of its functionality may be provided by other modules 50, 52, 54, 56, and/or 58. As another example, processor 20 may be configured to execute one or more additional modules that may perform some or all of the functionality attributed below to one of modules 50, 52, 54, 56, and/or 58.

Parameter module 50 is configured to determine one or more parameters within system 10. The one or more parameters within system 10 may comprise gas parameters related to the pressurized flow of breathable gas, and/or other parameters. Parameter module 50 is configured to determine the one or more parameters based on the output signals of sensors 18. The information determined by parameter module 50 may be used for controlling pressure generator 14, stored in electronic storage 24, and/or used for other uses. The one or more gas parameters of the pressurized flow of breathable gas may comprise, for example, one or more of a flow rate, a volume, a pressure, humidity, temperature, acceleration, velocity, and/or other gas parameters.

In some embodiments, parameter module 50 may be configured to determine the respiratory phase (e.g., inhalation, exhalation) during breathing of subject 12. The respiratory phase determinations made by parameter module 50 are based on the output signals from sensors 18, parameter information determined by parameter module 50, and/or other information. Parameter module 50 may be configured to determine additional breathing parameters related to the respiration of subject 12. Additional breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. The respiratory phase determinations may be used by control module 54 to control pressure generator 14 to control the pressurized flow of breathable gas delivered to subject 12, may be stored in electronic storage 24, and/or used for other uses. In some embodiments, parameter module 50 is configured to determine the respiratory phase (e.g., inhalation, exhalation) based on changes in pressure, flow rate, and/or other parameters determined by parameter module 50.

Leak module 52 is configured to estimate a current leak value. The current leak value may be an instantaneous indication of the amount of leak in system 10. The current leak value may be estimated based on one or more of the gas parameters determined by parameter module 50, a therapeutic level of a gas parameter, known properties of subject interface 16 (e.g., of conduit 30 and/or interface appliance 32), and/or other parameters, properties, or variables. The current leak value may be estimated based on a total flow rate, for example. The total flow rate may include a therapeutic flow rate delivered to subject 12 during inhalation and/or exhalation, and leak. The estimated current leak value may include intentional leak (e.g., to prevent rebreathing) and/or unintentional leak (e.g., mask or mouth leak).

Control module 54 is configured to control operation of pressure generator 14 to generate the pressurized flow of breathable gas according to a limited flow mode respiratory therapy regime. The limited flow mode respiratory therapy regime dictates therapeutic levels of a first gas parameter of the one or more gas parameters at or near the airway of the subject. In some embodiments, the limited flow mode respiratory therapy regime may dictate therapeutic levels of parameters in addition to the first gas parameter. Control module 54 is configured to control pressure generator 14 based on information related to the output signals from sensors 18, information determined by parameter module 50, information entered by a user to user interface 22, and/or other information. The pressurized flow of breathable gas generated by the pressure generator is controlled to replace and/or compliment a patient's regular breathing.

In some embodiments, control module 54 is configured such that the first gas parameter is a pressure. In some embodiments, control module 54 is configured such that the first gas parameter is a flow rate. In some embodiments, control module 54 is configured such that the first gas parameter is a parameter other than a pressure and/or a flow rate. Control module 54 may be configured to receive information associated with control inputs related to whether the first gas parameter is a flow rate, a pressure, and/or other parameters entered and/or selected by a user (e.g., subject 12) via user interface 22, and/or other devices. Control module 54 may be configured such that the received information indicates whether the first gas parameter is a flow rate, a pressure, and/or other parameters.

In some embodiments, control module 54 may be configured to control pressure generator 14 to generate the flow of gas in accordance with a ventilation and/or positive airway pressure support therapy regime in addition to and/or instead of the limited flow mode respiratory therapy regime. By way of non-limiting example, control module 54 may control pressure generator 14 such that the pressure support provided to the subject via the flow of gas comprises continuous positive airway pressure support (CPAP), bi-level positive airway pressure support (BPAP), proportional positive airway pressure support (PPAP), and/or other types of pressure support therapy.

Compensation module 56 is configured to determine a compensation amount to adjust the first gas parameter to compensate for respiratory effort during inhalation. Compensation module 56 is configured to determine the compensation amount such that the therapeutic levels for the first gas parameter are maintained. Control module 54 is configured to control pressure generator 14 to generate the pressurized flow of breathable gas with the first gas parameter at a level that reflects the compensation amount.

Compensation module 56 is configured to determine the compensation amount based on the therapeutic levels and the output signals. For example, the limited flow mode respiratory therapy regime may dictate therapeutic levels for a pressure. The output signals from sensors 18 may convey information related to an actual pressure. The actual pressure may be determined by parameter module 50. The actual pressure may vary with respiratory effort exerted by subject 12. Compensation module 56 may determine a compensation amount to adjust the pressure that corresponds to differences between the actual pressure and the therapeutic pressure. In some embodiments, compensation module 56 may be configured such that lower compensation amounts are determined for actual pressures that are closer to therapeutic levels, and higher compensation amounts are determined for actual pressures that are farther from therapeutic levels.

Compensation module 56 may be configured to determine one or more compensation amounts during an inhalation and/or during an exhalation. In some embodiments, the compensation amount determinations may be continuous during the limited flow respiratory therapy. The number and/or nature (e.g., continuous) of compensation amounts determined by compensation module 56 may be configurable by a user (e.g., a doctor, a caregiver, subject 12) via user interface 22, and/or other components of system 10. Control module 54 may be configured to control pressure generator 14 to generate the pressurized flow of breathable gas with the first gas parameter at levels that reflect the number and/or nature of the compensation amounts.

Compensation limit module 58 is configured to determine a compensation limit for the compensation amount of the first gas parameter. Compensation limit module 58 is configured to determine the compensation limit based on the current leak value. Compensation module 56 is configured to implement the compensation limit as a limit for the compensation amount. In some embodiments, compensation limit module 58 may be configured to determine a compensation limit based on the current leak value via an algorithm. The current leak value may be an input into the algorithm. The algorithm may be determined at manufacture, set and/or adjust by a user via user interface 22, and/or determined by other methods. In some embodiments, compensation limit module 58 may be configured to determine the compensation limit based on previous respiration by subject 12. In some embodiments, the compensation limit may be entered and/or selected by a user via user interface 22. In some implementations, compensation limit module 58 may be configured to titrate the compensation limit based on preferences of subject 12 (e.g., to increase comfort during therapy).

As described above, the first gas parameter may comprise a pressure, a flow rate, and/or other gas parameters. Determining a compensation limit for the compensation amount of the flow rate or the pressure based on the current leak value (compensation limit module 58), and implementing the flow rate or the pressure compensation limit as a limit for the compensation amount (compensation module 56), achieves limited flow respiratory therapy that ensures that an effective therapeutic pressure is maintained, but during inspiration (e.g., when the flow rate is greater than leak), that additional flow (above therapeutic levels) is not compensated for. This achieves the desired limited flow respiratory therapy while providing a smooth and comfortable flow rate and pressure profile to subject 12.

In some embodiments, compensation limit module 58 is configured to determine a flow rate compensation limit. In some embodiments, compensation limit module 58 is configured to determine a flow rate compensation limit that is one to two times the current leak value. Compensation limit module 58 is configured to determine the flow rate compensation limit as shown below:

$$\text{Flow Rate Compensation}_{limit} = [X] \times \text{current leak}$$

where $[X] = \{X \in \text{any real number} | 1 \leq X \geq 2\}$

By way of a non-limiting example, during inspiration, responsive to compensation module 56 implementing the flow rate compensation limit, as the compensated flow rate reaches the flow rate compensation limit, control module 54 may control pressure generator 14 to reduce a subject interface 16 mask (for example) pressure. During expiration, the flow rate may be lower than and/or approximately equal to the leak value, such that system 10 may provide therapeutic pressure compensation.

In some embodiments, compensation limit module 58 is configured to determine a pressure compensation limit. In some embodiments, compensation limit module 58 is configured to determine a pressure compensation limit that is a function of one to two times the current leak value. Compensation limit module 58 is configured to determine the pressure compensation limit as shown below:

$$\text{Pressure Compensation}_{limit} \approx f([X] \times \text{current leak})$$

where $[X] = \{X \in \text{any real number} | 1 \leq X \geq 2\}$

In this embodiment, the pressure compensation is limited to a maximum of the pressure compensation limit value. The pressure compensation limited embodiments differ from the embodiments wherein the flow rate compensation is limited because, in the pressure compensation limited embodiments, the flow rate limiting occurs indirectly as a result of limiting the compensated pressure. In the flow rate compensation limited embodiments, the flow rate compensation is limited directly, before the pressure compensation limit determination.

User interface 22 is configured to receive entry and/or selection of control inputs from subject 12 and/or other users that select whether system 10 operates in the flow compensation limit mode or the pressure compensation limit mode. Other users may comprise a caregiver, a doctor, a decision maker, and/or other users. This enables data, cues, results, and/or instructions and any other communicable items, collectively referred to as "information," to be communicated between a user (e.g., subject 12) and one or more of pressure generator 14, processor 20, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Figure 2:
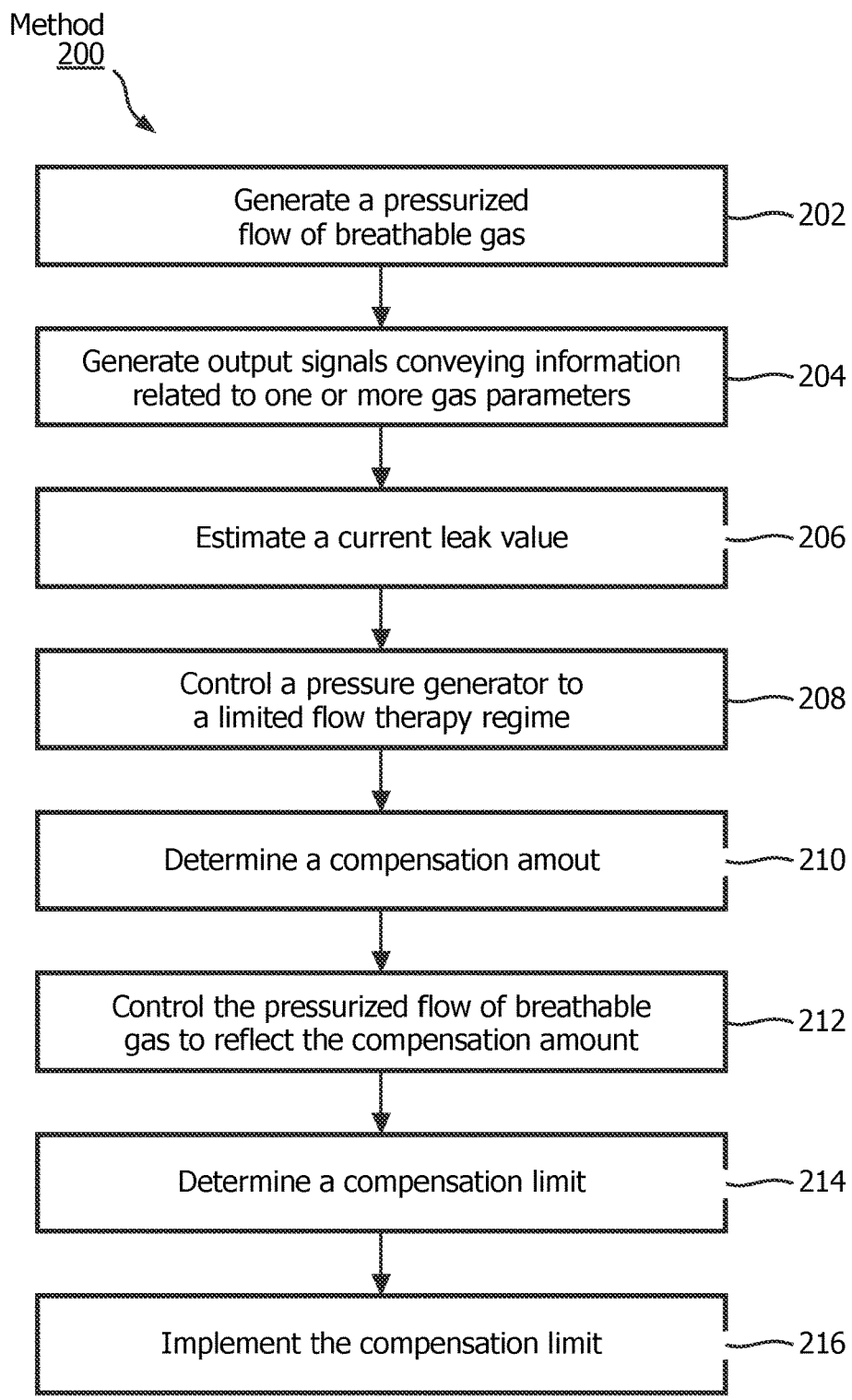
FIG. 2 illustrates a method for delivering a pressurized flow of breathable gas to the airway of a subject with a pressure support system.

FIG. 2 illustrates a method 200 for delivering a pressurized flow of breathable gas to the airway of a subject with a pressure support system. The pressure support system comprises a pressure generator, one or more sensors, and/or one or more processors. The one or more processors are configured to execute computer program modules. The computer program modules comprise a leak module, a control module, a compensation module, and a compensation limit module. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, the pressurized flow of breathable gas is generated. In some embodiments, operation 202 is performed by a pressure generator the same as or similar to pressure generator 14 (shown in FIG. 1 and described herein).

At an operation 204, output signals conveying information related to one or more gas parameters of the pressurized flow of breathable gas are generated. In some embodiments, operation 204 is performed by sensors the same as or similar to sensors 18 (shown in FIG. 1 and described herein).

At an operation 206, a current leak value may be estimated. In some embodiments, operation 206 is performed by a computer program module the same as or similar to leak module 52 (shown in FIG. 1 and described herein).

At an operation 208, the pressure generator may be controlled according to a limited flow therapy regime. Operation of the pressure generator may be controlled to generate the pressurized flow of breathable gas according to the limited flow mode therapy regime. The limited flow mode therapy regime may dictate a therapeutic level of a first gas parameter of the one or more gas parameters at or near the airway of the subject. In some embodiments, operation 208 is performed by a computer program module the same as or similar to control module 54 (shown in FIG. 1 and described herein).

At an operation 210, a compensation amount may be determined. The compensation amount may be an amount to adjust the first gas parameter to compensate for respiratory effort during inhalation to maintain the therapeutic level for the first gas parameter. Determining the compensation amount is based on the therapeutic level and the output signals. In some embodiments, operation 210 is performed by a computer program module the same as or similar to compensation module 56 (shown in FIG. 1 and described herein).

At an operation 212, the pressurized flow of breathable gas is controlled to reflect the compensation amount. Generation of the pressurized flow of breathable gas may be controlled such that the first gas parameter is maintained at a level that reflects the compensation amount. In some embodiments, operation 212 is performed by a computer program module the same as or similar to control module 54 (shown in FIG. 1 and described herein).

At an operation 214, a compensation limit may be determined. The compensation limit may be determined for the compensation amount of the first gas parameter. The compensation limit may be determined based on the current leak value. In some embodiments, operation 214 is performed by a computer program module the same as or similar to compensation limit module 58 (shown in FIG. 1 and described herein).

At an operation 216, the compensation limit may be implemented. The compensation limit may be implemented as a limit for the compensation amount. In some embodiments, operation 216 is performed by a computer program module the same as or similar to compensation module 56 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A pressure support system configured to deliver a pressurized flow of breathable gas to the airway of a subject, the pressure support system comprising:
a pressure generator configured to generate the pressurized flow of breathable gas;
one or more sensors configured to generate output signals conveying information related to one or more gas parameters of the pressurized flow of breathable gas; and
one or more processors configured to execute computer program modules, the computer program modules comprising:
a leak nodule configured to estimate a current leak value;
a control module configured to control operation of the pressure generator to generate the pressurized flow of breathable gas according to a limited flow mode therapy regime that dictates a therapeutic level of a first gas parameter of the one or more gas parameters at or near the airway of the subject;
a compensation module configured to determine a compensation amount to adjust the first gas parameter to compensate for respiratory effort to maintain the therapeutic level for the first gas parameter, wherein the compensation module is configured to determine the compensation amount based on the therapeutic level and the output signals;
wherein the control module is configured to control the pressure generator to generate the pressurized flow of breathable gas with the first gas parameter at a level that reflects the compensation amount; and
a compensation limit module configured to determine a compensation limit for the compensation amount of the first gas parameter as a function of the current leak value;
wherein the compensation module is configured to implement the compensation limit as a limit for the compensation amount.

2. The system of claim 1, wherein the control module is configured such that the first gas parameter is a flow rate.

3. The system of claim 2, wherein the compensation limit module is configured to determine a flow rate compensation limit that is one to two times the current leak value.

4. The system of claim 1, wherein the control module is configured such that the first gas parameter is a pressure.

5. The system of claim 4, wherein the compensation limit module is configured to determine a pressure compensation limit that is a function of one to two times the current leak value.

6. The system of claim 1, wherein the control module is configured such that the first gas parameter is a flow rate, and wherein the compensation module is configured to implement the compensation limit as a limit for the compensation amount such that the therapeutic level of the flow rate is maintained, but during inspiration, responsive to an inhalation flow that exceeds the current leak value, additional flow above the therapeutic flow rate is not compensator for.

7. The system of claim 1, wherein the compensation limit module is further configured to determine the compensation limit for the compensation amount of the first gas parameter based on previous respiration by the subject, determine the compensation limit for the compensation amount of the first gas parameter based on entries and/or selections of the compensation limit made via a user interface, and/or titrate the compensation limit based on preferences of the subject.

8. A method for delivering a pressurized flow of breathable gas to the airway of a subject with a pressure support system, the pressure support system comprising a pressure generator, one or more sensors, and one or more processors, the one or more processors configured to execute computer program modules, the computer program modules comprising a leak module, a control module, a compensation module, and a compensation limit module, the method comprising:
generating the pressurized flow of breathable gas with the pressure generator;
generating output signals conveying information related to one or more gas parameters of the pressurized flow of breathable gas with the one or more sensors;
estimating a current leak value with the leak module;
controlling, with the control module, operation of the pressure generator to generate the pressurized flow of breathable gas according to a limited flow mode therapy regime that dictates a therapeutic level of a first gas parameter of the one or more gas parameters at or near the airway of the subject;
determining a compensation amount, with the compensation module, to adjust the first gas parameter to compensate for respiratory effort to maintain the therapeutic level for the first gas parameter, wherein determining the compensation amount is based on the therapeutic level and the output signals;
controlling, with the control module, generation of the pressurized flow of breathable gas with the first gas parameter at a level that reflects the compensation amount;
determining a compensation limit, with the compensation limit module, for the compensation amount of the first gas parameter as a function of the current leak value; and
implementing, with the compensation module, the compensation limit as a limit for the compensation amount.

9. The method of claim 8, wherein the first gas parameter is a flow rate.

10. The method of claim 9, further comprising determining a flow rate compensation limit that is one to two times the current leak value.

11. The method of claim 8, wherein the first gas parameter is a pressure.

12. The method of claim 11, further comprising determining a pressure compensation limit that is a function of one to two times the current leak value.

13. The method of claim 8, wherein the first gas parameter is a flow rate, and wherein the compensation limit is implemented as a limit for the compensation amount such that the therapeutic level of the flow rate is maintained, but during inspiration, responsive to an inhalation flow that exceeds the current leak value, additional flow above the therapeutic flow rate is not compensator for.

14. The method of claim 8, further comprising determining the compensation limit for the compensation amount of the first gas parameter based on previous respiration by the subject, determining the compensation limit for the compensation amount of the first gas parameter based on entries and/or selections of the compensation limit made via a user interface, and/or titrating the compensation limit based on preferences of the subject.

15. A pressure support system configured to deliver a pressurized flow of breathable gas to the airway of a subject, the pressure support system comprising:
   means for generating the pressurized flow of breathable gas;
   means for generating output signals conveying information related to one or more gas parameters of the pressurized flow of breathable gas; and
   means for executing computer program modules, the computer program modules comprising:
   means for estimating a current leak value;
   means for controlling operation of the means for generating the pressurized flow of breathable gas to generate the pressurized flow of breathable gas according to a limited flow mode therapy regime that dictates a therapeutic level of a first gas parameter of the one or more gas parameters at or near the airway of the subject;
   means for determining a compensation amount to adjust the first gas parameter to compensate for respiratory effort to maintain the therapeutic level for the first gas parameter, wherein the means for determining a compensation amount is configured to determine the compensation amount based on the therapeutic level and the output signals;
   wherein the means for controlling operation is configured to control the means for generating the pressurized flow of breathable gas to generate the pressurized flow of breathable gas with the first gas parameter at a level that reflects the compensation amount; and
   means for determining a compensation limit for the compensation amount of the first gas parameter as a function of the current leak value;
   wherein the means for determining a compensation is configured to implement the compensation limit as a limit for the compensation amount.

16. The system of claim 15, wherein the means for controlling operation is configured such that the first gas parameter is a flow rate.

17. The system of claim 16, wherein the means for determining a compensation limit is configured to determine a flow rate compensation limit that is one to two times the current leak value.

18. The system of claim 15, wherein the means for controlling operation is configured such that the first gas parameter is a pressure.

19. The em of claim 18, wherein the means for determining a compensation limit is configured to determine a pressure compensation limit that is a function of one to two times the current leak value.

20. The system of claim 15, wherein the first gas parameter is a flow rate, and wherein the compensation limit is implemented as a limit for the compensation amount such that the therapeutic level of the flow rate is maintained, but during inspiration, responsive to an inhalation flow that exceeds the current leak value, additional flow above the therapeutic flow rate is not compensator for.

21. The system of claim 15, wherein the means for determining a compensation limit is further configured to determine the compensation limit for the compensation amount of the first gas parameter based on previous respiration by the subject, determine the compensation limit for the compensation amount of the first gas parameter based on entries and/or selections of the compensation limit made via a user interface, and/or titrate the compensation limit based on preferences of the subject.

* * * * *